United States Patent
Santhanam et al.

(10) Patent No.: US 6,379,716 B2
(45) Date of Patent: Apr. 30, 2002

(54) ECHINACEA EXTRACT AS ANTI-IRRITANT AND ANTI-AGING BOOSTER IN COSMETIC COMPOSITIONS

(75) Inventors: Uma Santhanam, Tenafly; Ronni Lynn Weinkauf, Oradell, both of NJ (US); Laura Rose Palanker, Midvale, UT (US); Bijan Harichian, Warren; Victor De Florio, Cranford, both of NJ (US)

(73) Assignee: Unilever Home & Personal Care USA, a division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/798,592

(22) Filed: Mar. 2, 2001

Related U.S. Application Data

(60) Provisional application No. 60/187,361, filed on Mar. 6, 2000.

(51) Int. Cl.$^7$ ................................................ A01N 37/00
(52) U.S. Cl. ...................................... 424/737; 514/557
(58) Field of Search .......................... 424/737; 514/557

(56) References Cited

U.S. PATENT DOCUMENTS

| | | | |
|---|---|---|---|
| 5,547,988 A | * 8/1996 | Yu et al. | |
| 5,667,791 A | 9/1997 | Hersh et al. | ................. 424/401 |
| 5,705,170 A | 1/1998 | Kong et al. | ................. 424/401 |
| 5,804,168 A | 9/1998 | Murad | ......................... 424/59 |
| 5,939,457 A | * 8/1999 | Miser | |

* cited by examiner

Primary Examiner—Christopher R. Tate
Assistant Examiner—Randall Winston
(74) Attorney, Agent, or Firm—Ellen Plotkin

(57) ABSTRACT

Echinacea extract in cosmetic skin care compositions, as anti-irritant, to reduce skin irritation caused by hydroxy acids, and to boost the anti-aging efficacy of hydroxy acids.

6 Claims, No Drawings

ECHINACEA EXTRACT AS ANTI-IRRITANT AND ANTI-AGING BOOSTER IN COSMETIC COMPOSITIONS

This application claims the benefit of U.S. provisional application No. 60/187,361 filed Mar. 6, 2000.

FIELD OF THE INVENTION

Use of echinacea to reduce irritation and boost anti-aging efficacy of cosmetic compositions containing hydroxy acids.

BACKGROUND OF THE INVENTION

Some ingredients used in topical products are potentially irritating, especially to people with "sensitive skin."

As an example, hydroxy acids (HAs) have been proven to deliver cosmetic benefits, such as improvement in the appearance of photodamaged or naturally aged skin, skin lightening, treatment of age spots, etc. Unfortunately, their use at high concentrations may occasionally be associated with skin irritation, e.g. skin redness and stinging sensation upon application. The irritation can be ameliorated by lowering the amount of an active ingredient in the composition or by reducing the active's penetration through the skin. A serious drawback of both approaches is that the efficacy is impaired. The HA related irritation can be reduced by raising the composition's pH but this method yields reduced efficacy due to a decreased HA penetration through the skin. It is desirable to reduce or eliminate the irritation potential of HAs while maintaining their efficacy.

The need exists, therefore, for a composition and method that prevents or reduces the skin irritation which may be caused by hydroxy acids.

U.S. Pat. No. 5,705,170 (Kong et al.) discloses an herbal cellulite treatment and a cosmetic composition which may contain from 0.1 to 20% wt. of an alpha hydroxy acid. The composition has a pH of from 3–6; echinacea extract is used in the example at a level of 2%. U.S. Pat. No. 5,667,791 (Hersh et al.) discloses a topical composition which may be in the form of a lotion, cream, oil or gel. One of the exemplified compositions contains 0.047% of echinacea and 0.018% of lactic acid. The compositions are used to reduce and repair X-ray radiation induced skin damage. U.S. Pat. No. 5,804,168 (Murad) discloses a composition which may be in the form of cream, paste, gel or ointment or emulsion and may be applied topically for treatment of sun-damaged skin. The composition may contain echinacea and lactic acid. The latter is used in the example at the level of 5.6% wt.

SUMMARY OF THE INVENTION

The present invention provides a method for reducing skin irritation caused by the topical application of a composition containing HAs, the method comprising topically applying echinacea extract. Echinacea extract may be co-present with HAs in the same composition, or may be applied from a separate composition.

According to the present invention, by virtue of topical application of echinacea extract, the skin irritation caused by HAs is reduced or eliminated.

Furthermore, it has been found according to the present invention that echinacea has an additional valuable effect of significantly boosting the anti-aging efficacy of HAs. Thus, when echinacea extract is present in the composition, HAs can be used in a lower amount, without reduction in efficacy, and thus reducing skin irritation potential even further.

The present invention also includes a cosmetic skin care composition containing HAs and *Echinacea purpurea* or *Echinacea pallida*.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the composition, unless otherwise specified.

Echinacea extract is employed in the inventive compositions to reduce or eliminate the skin irritation caused by HAs and/or to boost anti-aging effect of HAs. Echinacea extract, also known as Coneflower extract, can be purchased from commercial suppliers such as BioBotanica. Echinacea extract is used in the inventive compositions and methods in a concentration of from 0.1 to 20%; preferably from 0.5 to 10%, most preferably from 0.5 to 5%.

Echinacea extract may be obtained from the following echinacea species: *Echinacea angustifolia*, *Echinacea purpurea*, *Echinacea pallida*. *Echinacea purpurea* is preferred according to the present invention since it contains chicoric acid, which was shown, as part of the present invention to have anti-irritant activity. *Echinacea purpurea* is also commercially available. *Echinacea pallida* also contains chocoric acid, but it is not commercially available.

The hydroxy acid can be chosen from alpha-hydroxy acids, beta-hydroxyacids (e.g. salicylic acid), other hydroxy-carboxylic acids (e.g., dihydroxycarboxylic acid, hydroxy-dicarboxylic, hydroxytricarboxylic) and mixtures thereof or combination of their stereoisomers (DL, D or L).

Preferably the hydroxy acid is chosen from alpha-hydroxy acids having the general structure (1)

(1)

where M is H or a saturated or an unsaturated, straight or branched hydrocarbon chain containing from 1 to 27 carbon atoms.

Even more preferably the hydroxy acid is chosen from lactic acid, 2-hydroxyoctanoic acid, hydroxylauric acid, glycolic acid, and mixtures thereof. When stereo isomers exist, L-isomer is most preferred.

It is to be understood that depending on the pH of the composition, the hydroxy acid may be present as a salt, e.g. ammonium or potassium or sodium salt.

Although echinacea extract may be included into compositions that have any pH in the general range of 2.5 to 10, the inventive methods are particularly useful when compositions are at an acidic pH (especially if they contain a hydroxy acid), preferably 3–5 and most preferably at a pH of 3–4, because such compositions are particularly irritating.

A particular advantage of the inventive methods is that higher amounts of hydroxy acids may be employed without causing skin irritation. Preferably the amount of the hydroxy acid component present in the composition is from 0.01 to 20%, more preferably from 2 to 12% and most preferably from 4 to 12% by weight.

Glycolic acid and/or lactic acid are most preferred because although these ingredients have been found to cause irritation, they were found to be particularly efficacious at delivering cosmetic benefits.

The compositions and methods according to the invention also comprise a cosmetically acceptable vehicle to act as a diluent, dispersant or carrier for the active ingredients in the composition, so as to facilitate their distribution when the composition is applied to the skin.

Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition. The amount of vehicle may range from about 2 to about 99 wt %, preferably from about 50 to about 99%, most preferably from about 80 to 99%, by weight of the total composition.

According to the present invention, the vehicle is preferably at least 60 wt. % water, by weight of the vehicle. The inventive compositions are preferably oil-in-water emulsions, in order to improve dermal delivery of hydroxy acids (See Sah A., "An in-vitro study of the effect of formulation variables and product structure on the delivery of alpha-hydroxy acid (Lactic acid) to skin", MS Thesis, Department of Pharmaceutical Sciences of the College of Pharmacy, University of Cincinnati, Ohio, July 1996). Such improved delivery is frequently accompanied by increased irritation/sting, making the use of echinacea extract in such emulsions particularly critical. In the preferred oil-in-water emulsions according to the present invention, water comprises at least 50 wt. % of the inventive emulsion, most preferably from 50 to 70 wt. %, by weight of the composition.

Optional Skin Benefit Materials and Cosmetic Adjuncts

Various types of active ingredients may be present in cosmetic compositions of the present invention. Actives are defined as skin benefit agents other than emollients and other than ingredients that merely improve the physical characteristics of the composition. Although not limited to this category, general examples include anti-wrinkle compounds and sunscreens and tanning agents.

Sunscreens include those materials commonly employed to block ultraviolet light. Illustrative compounds are titanium dioxide, the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B.F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other component materials may range anywhere from 0.001% up to 20% by weight of the composition.

Use of the Composition

The composition according to the invention is intended primarily as a product for topical application to human skin, especially as an agent for conditioning and smoothening the skin, and preventing or reducing the appearance of wrinkled, aged and/or photodamaged skin, or lightening or evening of skin color and tone.

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

The following specific examples further illustrate the invention, but the invention is not limited thereto.

EXAMPLE 1

Prostaglandins such as PGE2 play a central role in inflammation and are therefore pertinent to the pathogenesis and treatment of irritation. It is known that cytokines such as IL-1 can cause an increase in PGE2 (Kupper T, in Immunology: The Role of Cells and Cytokines in Immunity and Inflammation" Oppenheim J J and Shevach E J, eds. Oxford University press, New York, 1990, pp 285–305).

The following example demonstrates that echinacea extract can effectively inhibit the induction of PGE2 caused by IL-1 which is increased by AHAS. Therefore, echinacea extract would be effective in reducing the irritation caused by HAs.

Neonatal human dermal fibroblasts (passage 5–9) were seeded at a density of 7500 cells per well in 96-well tissue culture treated plates (Corning-Costar, Corning, N.Y.). The medium used was Dulbecco's Modified Eagle's Medium (DMEM), high-glucose (Gibco/Life Technologies, Gaithersburg, Md.) supplemented with 2 mM L-glutamine, 10% fetal bovine serum, and antibiotic and anti mycotic solutions (all also Life Technologies). After 48 hours, each well was rinsed twice with 200 µl serum-free DMEM and the cells dosed with 200 µl in DMEM+L-glutamine containing IL-1α at 1 ng/ml+/−active. After six hours, cells were examined microscopically for qualitative viability, and the medium was harvested and frozen until analysis. Each treatment was run in quadruplicate.

Enzyme immunoassay was performed using a commercial PGE2 kit (Amersham, Buckinghamshire, England). PGE2-specific antibody is precoated on a set of microtiter wells. The assay is based on the competition between unlabelled PGE2 (standard or sample) and a fixed quantity of peroxidase labelled PGE2 for a limited amount of the well-bound PGE2-specific antibody. Standards of 0, 1, 2, 4, 8, 16, and 32 pg/well or 50 µl media/well were applied with 50 µl/well of 0.1 M phosphate buffer pH 7.5 for 3 hours at 4° C. At the end of this incubation, 50 µl/well of horseradish peroxidase-conjugated PGE2 was added to all wells and the plate incubated for 1 hour at 4° C. Plates were washed 4 times with 300 µl/well 0.01M phosphate buffer pH 7.5 containing 0.5% Tween 20. 150 µl/well 3,3',5,5'-tetramethylbenzidine/hydrogen peroxide substrate in 20% dimethylformamide was added and the plate incubated exactly 30 minutes at room temperature. Reaction was stopped by adding 100 µl/well 1M sulfuric acid. The Dynatech MR7000 microplate spectrophotometer (Dynatech, Chantilly, Va.) was used to quantitate color in the wells by reading absorbance at 450 nm. A standard curve was plotted and the amount of PGE2 in the samples was extrapolated from the curve.

The anti-inflammatory potential of the test compounds is assessed by the ability of the compound to inhibit IL-1 a-induced PGE2 and is expressed as the ratio of PGE2 produced by the cells treated with the test compound+IL-1a to PGE2 produced by the cells treated with IL-1a alone. The lower this ratio, the greater the anti-inflammatory activity. Statistical significance was determined using the student's t-test.

TABLE 1

| Treatment | Concentration | Ratio of $PGE_2$ produced by echinacea + IL-1a/IL-1a | p value vs IL-1a |
|---|---|---|---|
| Experiment 1 | | | |
| Echinacea purpurea extract | 0.1% | 0.2 | 0.05[a] |
| Echinacea purpurea extract | 0.01% | 0.6 | 0.05[a] |
| Experiment 2 | | | |
| Echinacea purpurea extract | 0.1% | 0.2[a] | 0.05[a] |
| Echinacea purpurea extract | 0.01% | 0.6 | >0.1 |

[a]: significant decrease in PGE2 production

It can be seen from the results in Table 1 that Echinacea extract significantly reduced IL-1a - induced PGE2 production in vitro.

Extract from another Echinacea species, named *E-angustofolia*, was also tested and it was significantly less active than *E-purpurea* (Table 1 a).

TABLE 1a

| Treatment | Concentration | Ratio of PGE2 produced by echinacea + 2L-1a/IL-1a | p value vs IL-1a |
|---|---|---|---|
| Echinacea purpurea | 0.1% | 0.18 | 0.006[a] |
| Echinacea angustofolia | 0.5% | 0.52 | 0.05[b] |

[a] significant decrease in PGE2 production compared to *Echinacea angustofolia*;
[b] significant decrease in PGE2 production compared to control Echinacea has been reported to contain various compounds including polysaccharides such as echinacosides and caffeic acid esters such as chicoric acid. In order to find out which compounds in the Echinacea extract may be contributing to the activity in the current assay, chicoric acid was tested in the PGE2 test and was found to be effective at 0.001%. (Table 1b).

TABLE 1b

| Treatment | Concentration | Ratio of PGE2 with echinacea + IL-1a/IL-1a | p value vs IL-1a |
|---|---|---|---|
| Chicoric acid | 0.001% | 0.02 | 0.002[a] |

[a]: significant decrease in PGE2 production

The chicoric acid content of *Echinacea purpurca* is in the range of 0.6–2.1%, (Botanicals, A Phytocosmetic Desk reference; F. S. D Amelio, Sr., CRC Press, 1999). From Table 1 above, it can be observed that at the effective concentration of Echinacea at 0.1%, chicoric acid content would be in the range of 0.0006%–0.002% and chicoric acid in this range was effective in reducing irritation.

Furthermore, it has been reported that while chicoric acid is abundant in *Echinacea purpurea*, it is practically absent in *Echinacea angustofolia* (Botanicals, A Phytocosmetic Desk reference; F. S. D Amelio, Sr., CRC Press, 1999). While *Echinacea pallida* is said to contain chicoric acid, its concentration is unknown. Furthermore, *Echinacea pallida* is not commercially available. Therefore, *E. purpurea* would be the preferred species.

EXAMPLE 2

Irritation Test Method

Four Exposure Patch Test: The objective was to compare the level of irritation produced by various test materials after repeated patch applications. The test materials were held in contact with the skin under occlusive conditions. The outer upper arm of the panelist was designated as the area of application. Bandage type dressing (Scanpor tape) was used to hold the patches (25 mm Hill Top Chamber fitted with 18 mm diameter disc of Webril padding) into place. Both upper arms of the panelist were used. Patches were applied in a balanced random order.

Patches were applied at 9:00 o'clock Monday morning and removed at 9:00 o'clock Tuesday morning (24 hour exposure). A new set of patches was applied at 3:00 o'clock Tuesday afternoon and removed Wednesday morning at 9:00 o'clock (18 hour exposure). A third set of patches was applied at 3:00 o'clock Wednesday afternoon and removed Thursday morning at 9:00 o'clock (18 hour exposure). A final set of patches was applied at 3:00 o'clock Thursday afternoon and removed Friday morning at 9:00 o'clock (18 hour exposure).

Each time the patches were removed, the sites were rinsed with warm water and patted dry. The test sites were then marked with a surgical skin marking pen to ensure location for grading and subsequent patch applications. Test sites were evaluated at 3:00 p.m. on Tuesday, Wednesday, Thursday, and Friday of the study, prior to re-patching.

Skin irritation such as moderate redness, dryness, and/or itching of the test site is expected. Swelling of the test sites was possible. If any test site had moderate redness or any swelling at any evaluation, that particular test site was not repatched.

The test sites on each arm were visually ranked by two trained examiner under consistent lighting. The test sites were ranked in order of severity. The examiner ranking responses at the first evaluation period continued ranking the sites each day throughout the study.

In ranking the reactions, the site with the most severe response was given the lowest score;. The site with the second most severe response was given the second lowest score, etc. There was no forced ranking. If two or more sites had no response or the same response (no difference between sites), an average of the ranks was assigned. If a site had been discontinued, due to degree of irritation, the site retained the rank it received at the time dosing was discontinued.

Statistical Analysis

The ranking results from the patch treatments were statistically compared by nonparametric statistical methods. The test materials containing the anti-irritants were compared to the corresponding control containing only hydroxy acid, using Friedman's Rank Sum at each evaluation point with the panelist acting as a block (i.e., each panelist was tested with each test treatment). A p-value of <0.10 was considered statistically significant.

Compositions containing ingredients as indicated in Table 3, were tested using the Irritation Test Method. 17 subjects were tested. The results that were obtained are summarized in Table 3. The higher the sum of ranks, the less is the irritation. *Echinacea purpurea* was used in the examples below.

| EMULSION BASE FORMULA | | |
|---|---|---|
| FULL CHEMICAL NAME OR CFTA NAME | TRADE NAME AND % ACTIVE | WT. % |
| water, DI | | 46.54 |
| disodium EDTA | Sequesterene Na2 | 0.05 |
| magnesium aluminum silicate | Veegum Ultra | 0.6 |
| methyl paraben | Methyl Paraben | 0.15 |
| simethicone | DC Antifoam Emulsion | 0.01 |
| butylene glycol 1,3 | Butylene Glycol 1,3 | 3.0 |
| hydroxyethylcellulose | Natrasol 250 HHR | 0.5 |
| glycerine, USP | Glycerine USP | 2.0 |
| xanthan gum | Keltrol 1000 | 0.2 |
| triethanalamine | Triethanolamine 99 (%) | 1.2 |
| stearic acid | Pristerene 4911 | 3.0 |
| propyl paraben NF | Propylparaben NF | 0.1 |
| glyceryl hydrostearate | Naturechem GMHS | 1.5 |
| stearyl alcohol | Lanette 18DEO | 1.5 |
| isostearyl palmitate | Protachem ISP | 6.0 |
| C12–15 alcohols octonoate | Hetester FAO | 3.0 |
| dimethicone | Silicone Fluid 200 (50 cts) | 1.0 |
| cholesterol NF | Cholesterol NF | 0.5 |
| sorbitan stearate | Sorbitan Stearate | 1.0 |
| butylated hydroxytoluene | Embanox BHT | 0.05 |
| tocopheryl acetate | Vitamin E Acetate | 0.1 |
| PEG-100 stearate | MYRJ 59 | 2.0 |
| sodium stearoyl lactylate | Pationic SSL | 0.5 |
| retinyl palmitate | Vit. A Palmitate 84% | 0.06 |
| hydroxy caprylic acid | Hydroxy caprylic acid | 0.1 |
| water, DI | | q.s. to 99.80 |
| alpha-bisabolol | Alpha-bisabolol | 0.2 |
| pH | | 7–8 |

Additional ingredients in the Examples below were added in place of water. pH was adjusted with ammonium hydroxide or hydrochloric acid. Glycolic acid was 70% active, as received.

TABLE 2a

| COMPOSITION | INGREDIENTS | IRRITATION SCORE (Day 4) |
|---|---|---|
| 1 | Base Formula | 60.5 |
| 2 | Base Formula + 8% Glycolic acid | 51.0 |
| 3 | Composition #2 + 1% Echinacea extract | 76.0[a] |

[a]: significantly less irritating than composition 2, p <0.05.

TABLE 2b

| COMPOSITION | INGREDIENTS | IRRITATION SCORE (Day 4) |
|---|---|---|
| 1 | Base Formula | 85.5 |
| 2 | Base Formula + 8% Glycolic acid | 57.5 |
| 3 | Composition #2 + 1% *Echinacea purpurea* extract | 84.0[a] |

[a]: significantly less irritating than composition 2, $p < 0.05$.

TABLE 2c

| COMPOSITION | INGREDIENTS | IRRITATION SCORE (Day 1) |
|---|---|---|
| 1 | Base Formula | 68.0 |
| 2 | Base Formula + 8% Glycolic acid | 42.5 |
| 3 | Composition #2 + 0.5% *Echinacea purpurea* extract | 62.0[a] |

[a]: significantly less irritating than composition 2, $p < 0.1$.

It can be seen from the results in Tables 2a,b,c that Echinacea extract (Composition 3) significantly reduced the irritation induced by composition #2 (containing 8% glycolic acid).

EXAMPLE 3

This example investigated the effect of echinacea on the skin anti-aging efficacy of glycolic acid.

Procedure: The study was a 12-week bilateral comparison use test of two formulations.

Subjects having a moderate degree of photodamaged skin on both forearms were enrolled in the study. A minimum of 15 qualified subjects per paired comparison completed the study. Product assignment was randomized and balanced for left/right usage across the subject pool. Subjects were instructed to use the appropriate product to the left/right arms at home and applied approximately 1 gram twice daily for 12 weeks. At Week 0 (before treatment began), week 4, 8, and 12, visual evaluation for photodamaged skin condition was conducted. Clinical (visual) assessments were conducted for photodamaged skin using the following 10 point scale:

0=none

1–3=mild 4–6=moderate 7–9=severe

The following paired comparisons were made:

Paired comparison I: base formulation A vs. base formulation A+8% glycolic acid Same base formulation A was used as in Example 2. *Echinacea purpurea* was used. Paired comparison II: base formulation A+8% glycolic acid vs base formulation A+8% glycolic acid 5% echinacea.

The Wilcoxon signed rank test, Pratt-Lehmann version, was used to statistically assess the magnitude of average change from baseline attributable to treatment, with subject acting as a block in this analysis. In addition, to compare the extent of change from baseline between the two treatments within a paired comparison, the nonparametric Wilcoxon signed-rank test, Pratt-Lehmann version, was also used.

The results that were obtained are summarized in Table 3A and 3B

TABLE 3A

Average improvement in Photodamaged Skin (Paired comparison I)

| Week | Base Formula | Base Formula + 8% glycolic acid |
|---|---|---|
| 0 | 0 | 0 |
| 4 | −0.14 | −0.17 |
| 8 | −0.41 | −0.44 |
| 12 | −0.64 | −0.72 |

TABLE 3B

Average Improvement in Photodamaged Skin (Paired comparison II)

| Week | Base formula A + 8% glycolic acid | Base formula A + 8% glycolic acid + 5% echinacea |
|---|---|---|
| 0 | 0 | 0 |
| 4 | −0.19 | −0.13 |
| 8 | −0.47 | −0.66** |
| 12 | −0.82 | −0.91 |

**Base formulation A + 8% glycolic + 5% echinacea provided significantly greater improvement than Base formulation A + 8% glycolic ($p < 0.05$)

Examples 4–8 illustrate topical compositions according to the present invention. The compositions can be processed in conventional manner. They are suitable for cosmetic use. In particular the compositions are suitable for application to wrinkled, rough, dry, flaky, aged and/or UV-damaged skin to improve the appearance and the feel thereof as well as for application to healthy skin to prevent or retard deterioration thereof.

EXAMPLE 4

A typical oil-in-water emulsion within the scope of the invention is as follows:

| chemical name | wt. % |
|---|---|
| propylene glycol | 1 |
| glycerin | 1 |

| chemical name | wt. % |
|---|---|
| hydroxyethylcellulose | 0.5 |
| magnesium aluminum silicate | 0.5 |
| imidazolidinyl urea | 0.5 |
| tetrasodium EDTA | 0.05 |
| petrolatum | 2 |
| isopropyl palmitate | 5 |
| dimethicone | 0.5 |
| cholesterol | 0.5 |
| cetyl alcohol | 0.5 |
| isostearic acid | 3 |
| peg-40 stearate | 1 |
| peg-100 stearate | 1 |
| sorbitan stearate | 1 |
| Echinacea | 1 |
| glycolic acid | 7 |
| ammonium hydroxide | to pH 4.0 |
| water DI | qs to 100% |

EXAMPLE 5

Another typical oil-in-water emulsion within the scope of the invention is as follows:

| chemical name | wt. % |
|---|---|
| propylene glycol | 1 |
| hydroxyethylcellulose | 0.5 |
| magnesium aluminum silicate | 0.5 |
| imidazolidinyl urea | 0.2 |
| petrolatum | 2 |
| isopropyl palmitate | 5 |
| dimethicone | 0.5 |
| cholesterol | 0.5 |
| stearic acid | 3 |
| isostearic acid | 1.5 |
| glycerol stearate | 1 |
| peg-40 stearate | 1 |
| peg-100 stearate | 1 |
| sorbitan stearate | 1 |
| cetyl alcohol | 0.5 |
| Echinacea | 2 |
| glycolic acid | 10 |
| ammonium hydroxide | to pH 3.8 |
| water DI | qs to 100% |

EXAMPLE 6

A typical water-in-oil dispersion within the scope of the invention is as follows:

| chemical name | wt. % |
|---|---|
| isostearyl neopentanoate | 20 |
| peg-8 caprylic/capric glycerides | 6 |
| cetyl octanoate | 17 |
| polyglyceryl-6 dioleate | 15 |
| cyclomethicone | 20 |
| glyceryl isostearate | 0.5 |
| isostearic acid | 0.5 |
| ceramide III | 0.1 |
| ppg-5-cetheth-20 | 3 |
| L-lactic acid/potassium lactate | 6 |
| hydroxycaprylic acid | 0.1 |
| Echinacea | 0.5 |
| water DI | q.s. to 100% |

EXAMPLE 7

The following oil-in-water emulsion within the scope of the invention is prepared:

| chemical name | wt. % |
|---|---|
| glycerin | 1 |
| tetrasodium EDTA | 0.1 |
| cetyl alcohol | 1 |
| stearyl aclcohol | 1 |
| mineral oil | 5 |
| dimethicone | 1 |
| cyclomethicone | 0.5 |
| dimethiconol | 0.2 |
| polyquaternium-37 | 2 |
| steareth-21 | 1 |
| steareth-2 | 0.5 |
| salicylic acid | 2 |
| Echinacea | 1.5 |
| triethanolamine to pH | 3.0 |
| water DI | qs to 100% |

EXAMPLE 8

The following oil-in-water emulsion within the scope of the invention is prepared:

| chemical name | wt. % |
|---|---|
| xanthan gum | 0.2 |
| disodium EDTA | 0.1 |
| sodium PCA | 0.5 |
| diazodinyl urea | 0.3 |
| titanium dioxide | 1 |
| stearic acid | 3 |
| cyclomethicone | 0.3 |
| cetyl alcohol | 0.5 |
| glyceryl stearate | 0.5 |
| peg-100 stearate | 0.5 |
| steareth-2 | 0.2 |
| lecithin | 0.5 |
| tocopherol | 0.2 |
| octyl methoxycinnamate | 6 |
| Echinacea | 2 |
| glycolic acid | 3 |
| malic acid | 2 |
| lactic acid | 2 |
| green tea extract | 1 |
| triethanolamine | to pH 3.8 |
| water DI | qs to 100% |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A method for preventing or reducing the appearance of human skin aging by topically applying to the human skin a cosmetic composition comprising:

(i) about 4% to about 12% by weight of a hydroxy acid compound;
  (ii) about 0.1% to about 20% by weight of *Echinacea purpurea* extract or *Echinacea pallida* extract; and
  (iii) a cosmetically acceptable vehicle.

2. The method according to claim 1 wherein the hydroxy acid compound is a salt of glycolic acid or lactic acid.

3. The method according to claim 1 wherein the hydroxy acid compound is glycolic acid or lactic acid.

4. The method according to claim 1 wherein the composition has a pH ranging from about 3 to about 5.

5. The method according to claim 1 wherein the composition is an oil-in-water emulsion.

6. The method according to claim 1 wherein the preventing or reducing of the appearance of human skin aging is with respect to a characteristic selected from the group consisting of wrinkles, evening skin color, evening tone and combinations thereof.

* * * * *